(12) United States Patent
Gotschim et al.

(10) Patent No.: US 6,261,229 B1
(45) Date of Patent: Jul. 17, 2001

(54) METHOD AND SYSTEM FOR GATHERING AND ANALYZING PSYCHOPHYSICS DATA

(75) Inventors: Christian Peter Gotschim, Boulder; Yue Qiao, Longmont, both of CO (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/354,535

(22) Filed: Jul. 15, 1999

(51) Int. Cl.⁷ ..................................................... A61B 5/00
(52) U.S. Cl. ................................................................. 600/300
(58) Field of Search ................................. 600/558, 587, 600/300

(56) References Cited

U.S. PATENT DOCUMENTS

| | | |
|---|---|---|
| 5,012,333 | 4/1991 | Lee et al. . |
| 5,412,773 | 5/1995 | Carlucci et al. . |
| 5,640,501 | 6/1997 | Turpin . |
| 5,640,580 | 6/1997 | Slayden et al. . |
| 5,659,770 | 8/1997 | Yamada . |
| 5,680,629 | 10/1997 | Slayden et al. . |
| 5,742,836 | 4/1998 | Turpin et al. . |
| 5,745,712 | 4/1998 | Turpin et al. . |
| 5,754,222 | 5/1998 | Daly et al. . |
| 5,809,266 | 9/1998 | Touma et al. . |

OTHER PUBLICATIONS

David Brainard et al., "Psychophysics Toolbox: Introduction", 1997, pp. 1–4.

*Primary Examiner*—Max Hindenburg
(74) *Attorney, Agent, or Firm*—Gary D. Mann; Konrad Raynes & Victor

(57) ABSTRACT

Disclosed is method, system, and program for defining and administering a test to determine human perceptions of observable samples, such as printed text or images, sounds, motion pictures, etc. A displayable test building window includes input fields to receive input on at least one observable sample according to at least one type of experiment. Generated in a data gathering window is at least one perception input field for each observable sample and at least one type of experiment. The observer is capable of entering perception information in each input field concerning the observable samples. Observer perception input on the observable samples is received and stored. Statistical analysis is then performed on the entered perception input.

28 Claims, 12 Drawing Sheets

METHOD AND SYSTEM FOR GATHERING AND ANALYZING PSYCHOPHYSICS DATA

BACKGROUND OF THE INVENTION

1. Field of the Invention

The present invention relates to a method and system for automating the process of conducting psychophysics experiments, including test set-up, test administration, and data analysis.

2. Description of the Related Art

Psychophysics is commonly defined as the quantitative branch of the study of perception, examining the relations between observed stimuli and responses and the reasons for those relations. Since its inception, psychophysics has been based on the assumption that the human perceptual system is a measuring instrument yielding results (experiences, judgments, responses) that may be systematically analyzed.

Because of its long history, its experimental methods, data analyses, and models of underlying perceptual and cognitive processes have reached a high level of refinement. For this reason, many techniques originally developed in psychophysics have been used to unravel problems in learning, memory, attitude measurement, and social psychology.

In the general paradigm of visual psychophysics, a human subject is presented with accurately controlled stimuli, and in certain prescribed ways, is asked what he sees. From the results of these experiments inferences can be made about the nature of visual processes.

In the printing industry visual psychophysics testing can be used wherein there is to be correlated human perceptions of print quality with physical measurements such as, for example, gray levels, halftone screening, density control, and the like. Five psychophysics testing methods which have been used in the printing and other display industries include the Paired Comparison, Ranking Order, Rating Scales, Ratio Scales and Categorical Scales methods.

The Paired Comparison method involves making pairs of all possible combinations of a group of different print samples. The sample pairs are shown to the observers who in turn select which one of each pair is of the higher visual print quality. The law of comparative judgments is applied to analyze the data. The results are shown with a table of data and graphs.

The Ranking Order method involves ranking all samples in order of quality. For example, if an observer was shown four images, the observer would be asked to rank them number 1 through 4, in order of quality. Number 1 would correspond to the best of the 4 images. Number 4 would correspond to the worst. Like the Paired Comparison method, the law of comparative judgments is applied to analyze the data.

The Categorical Scale method involves viewing each sample alone and not in comparison with others. The observer is asked to place each sample in a category which has been pre-defined by the experimenter. For example, the experimenter may set up the following image categories: (1) lowest imaginable quality, (2) low quality, (3) acceptable quality, (4) high quality, and (5) highest imaginable quality. The observer would be shown one sample at a time and instructed to place that sample in one of these five categories.

The Rating Scale method involves a comparison of a sample with two standards which are at both extremes of the quality scale. The observer is told that the one standard which is associated with the highest quality image is ranked number 10 on a 10 point scale. He is further told that the other standard which is associated with the lowest quality image is ranked 0 on the same scale. Finally, he is shown each of the samples, asked to compare each with the two standards and assign a numerical rating between 0 and 10 to each sample.

The Ratio Scale method is very similar to the Rating Scale method previously described. The only difference is that only one standard is used for purposes of comparison and assigning a numerical rating.

The above methods themselves and their statistical analysis are fully described in James Bartleson and Franc Grum, "Visual Measurements", which is Volume 5 in "Optical Radiation Measurements", Academic, Orlando, 1984; and J. P. Guilford, "Psychometric Methods," McGraw-Hill, $2^{nd}$ Edition, 1954, which publications are incorporated herein by reference in their entirety.

The process of conducting a psychophysics experiment is time and labor intensive. It involves the generation of the samples to be observed, the randomization of the samples, the observation of the samples by the test subjects, the collection of the observation data, and the statistical analysis of the data. Many experiments require 15 to 20 or more observers to view the samples. Thus an experimenter's job would involve generating the samples, randomizing the samples for each of the 15–20 observers, collecting the data during each of the 15–20 observation sessions, and conducting the statistical data analysis by hand.

Because of the time and labor intensive nature of this testing, there is a need to automate the process, thereby greatly reducing the testing time.

SUMMARY OF THE PREFERRED EMBODIMENTS

To overcome the limitations in the prior art described above, preferred embodiments disclose method, system, and program for defining and administering a test to determine human perceptions of observable samples. A displayable test building window includes input fields to receive input on at least one observable sample according to at least one type of experiment. Generated in a data gathering window is at least one perception input field for each observable sample and at least one type of experiment. The observer is capable of entering perception information in each input field concerning the observable samples. Observer perception input on the observable samples is received and stored. Statistical analysis is then performed on the entered perception input.

In preferred embodiments, the type of experiments included in the test may be a paired comparison, ranking order, categorical scale, rating scale, ratio scale, and probit analysis experiment. The observable sample that is the subject of the experiment may comprise images, text, sound, motion pictures, or any other media in which information may be embedded.

In further embodiments, a plurality of different types of experiments which the user selects to include in the test may be displayed in the test building window. In such case, the data gathering window would generate at least one input field for each observable sample and each type of experiment the user selects.

In still further embodiments, the test building window may further display an algorithm field indicating at least one algorithm used to generate each observable sample. In such case, the data gathering window would generate at least one input field for each observable sample printed according to each algorithm displayed in the algorithm field.

Preferred embodiments provide an improved method and apparatus for testing definition and generation using a GUI for graphically specifying data items and computations to be performed on the data. The present invention provides a psychophysics testing tool that uses objects to define both testing layout and the data aspects of the testing. Unlike the prior art, the present invention provides a graphical way to accomplish both of these testing aspects. That is, a GUI is used to facilitate all testing steps, including sample generation, randomization, observation, data collection, and analysis.

DETAILED DESCRIPTION OF THE PREFERRED EMBODIMENTS

Figure 1:
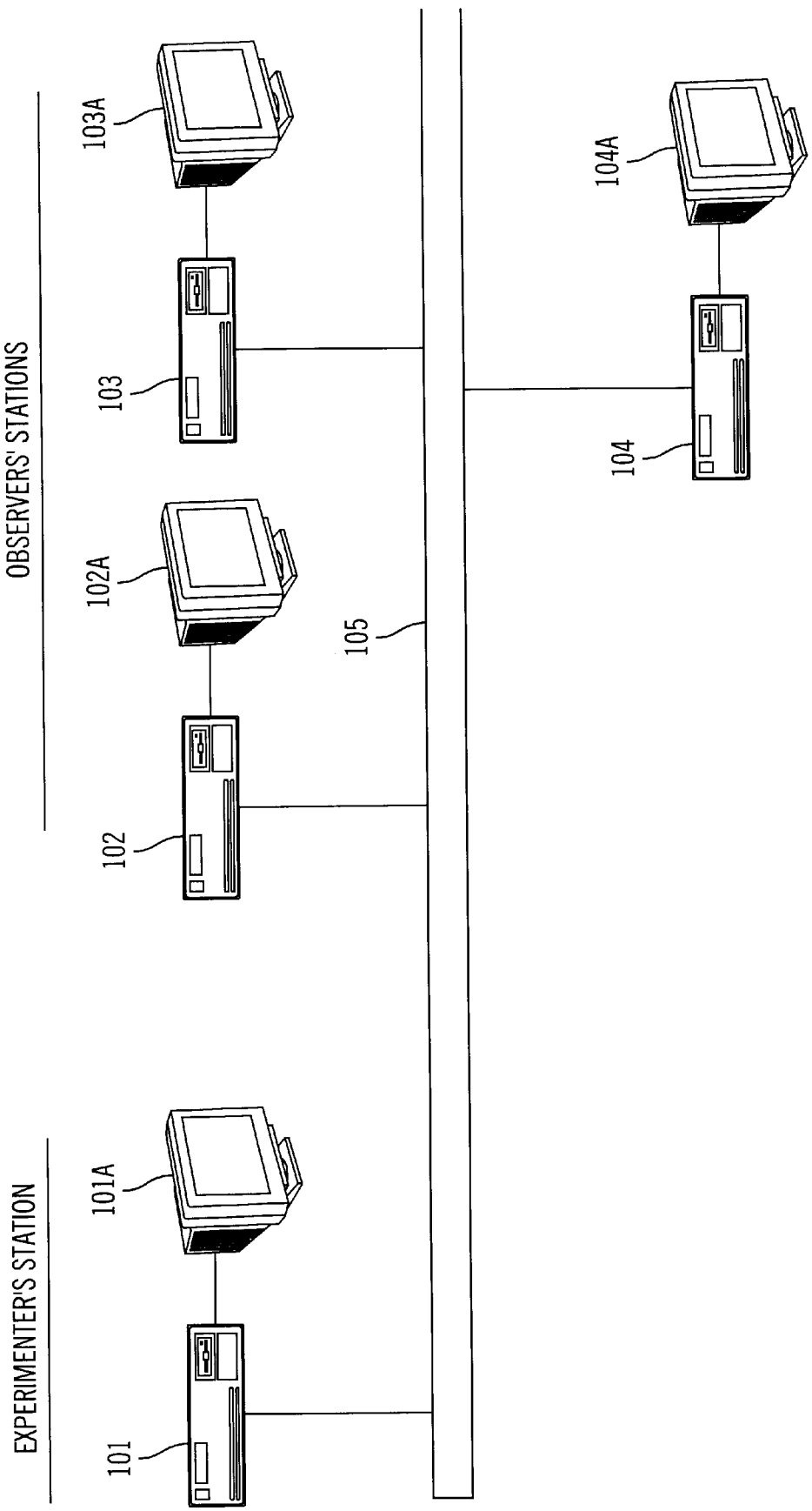
FIG. 1 is a block diagram illustrating a computing environment in which preferred embodiments of the present invention are implemented.
Figure 2:
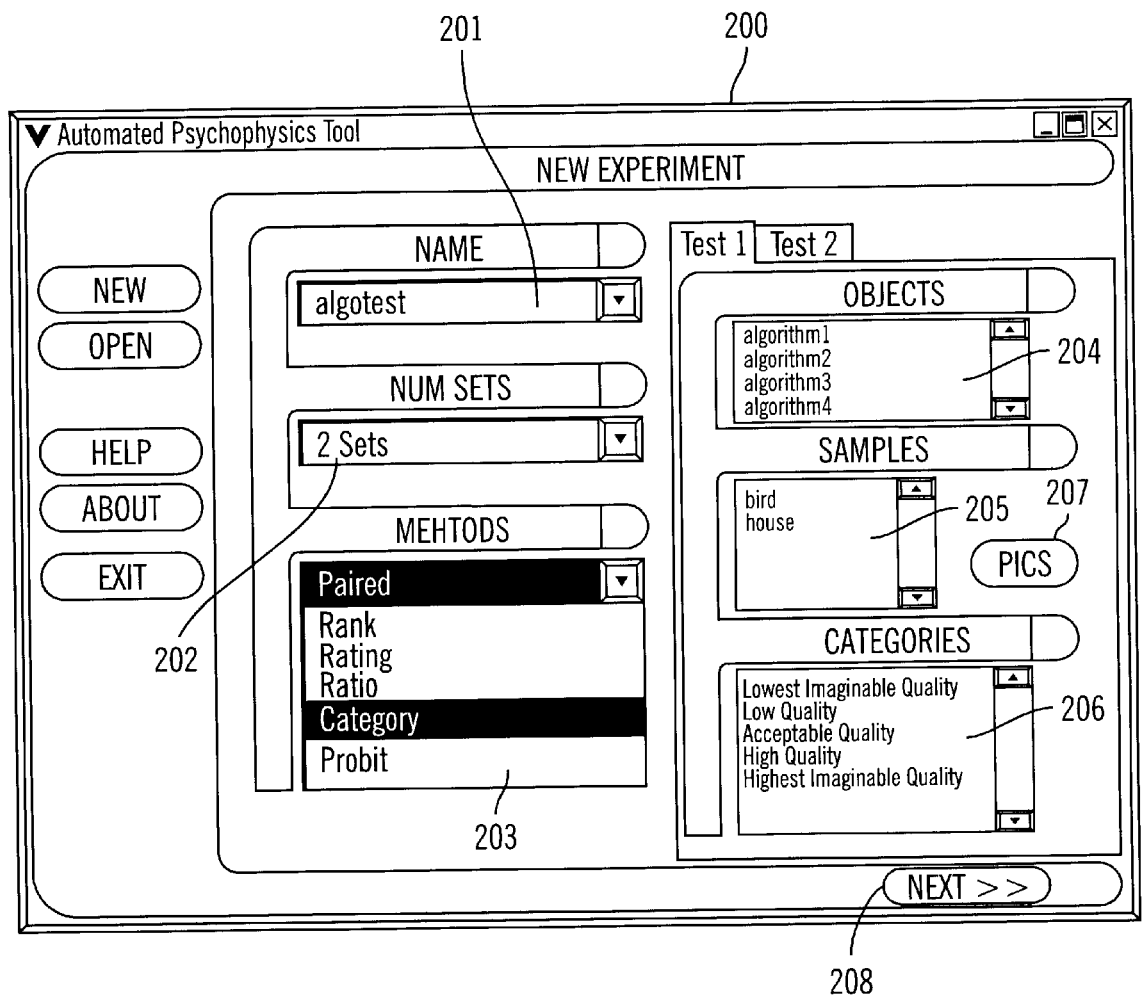
FIGS. 2, 3A, and 3B illustrate graphical user interface (GUI) panels displayed on a computer monitor to define a psychophysics experiment in accordance with preferred embodiments of the present invention.

The apparatus and method of this invention is useful for allowing the skilled artisan to collect data concerning the ability of humans (i.e. observers) to detect, recognize, discriminate or assign qualitative labels to either single objects or a group of objects. The invention then provides for the recordation of that observer's response to each sample. For example, the observer can indicate which of two or more samples he likes the best, or he can rank a group of samples in order of preference, etc. (i.e., provide a psychophysical response).

The preferred embodiment of this invention includes a computer means for collecting such responses, as well as for controlling the presentation of the stimulus to the observer. Thus, the computer means can track the subject's responses and use those responses to determine the statistical results. As a result, the automated nature of this invention can be continuously employed in a manner which is not highly labor intensive.

The observer can provide responses about the samples through the computer. It has been found that the practice of this invention is greatly facilitated by employing computers for communicating instructions and prompts to the observer, and receiving responses from the observer. Thus, it is preferred that the computer include a response means having a "mouse" or other suitable input capability for receiving responses from the observer. Such a capability not only eliminates the need for recording evaluations on a written ballot but also removes a potential directional influence on the subject due to the visual availability of previously recorded responses. In addition to the "mouse," computer systems for receiving responses or input are commercially available and include, for example, a touch sensitive computer monitor screen, a keyboard or similar means for positioning a cursor on the monitor screen and a bit pad with stylus.

As previously described, five psychophysics methods which have been used in the printing and other display industries include the Paired Comparison, Ranking Order, Rating Scales, Ratio Scales and Categorical Scales methods.

In addition to these known methods, this invention further includes a unique variation of a psychophysics method called the Probit Analysis method. Probit Analysis involves comparing a sample with one standard sample to query the observer as to which of the viewed samples has superior quality. A statistical technique is used for fitting a cumulative normal distribution to data.

Probit Analysis is useful for determining the threshold of print quality or image quality. In other words, it helps determine what is the threshold of a particular physical measurement to correlate with acceptable, unacceptable, or excellent print quality. For example, probit analysis could be used to measure the quality of print images having different amounts of print toner. This would help when selecting the toner level to use to print the image. Probit analysis may apply to selecting other physical quantities to use in printing, such as density control, color difference, and other physical dimensions or quantities that affect print quality.

The preferred embodiment of this invention is a graphical user interface (GUI) program which allows for test building, test taking, and data analysis for the above six psychophysics methods. Experimenters may build a test including one or more of the above testing methods to include multiple psychoanalysis tests in a single test package.

Preferred embodiments result in substantial time savings by allowing the experimenter to automatically build a test including different testing methods, generate samples for the test, order the samples, and provide for computerized test taking. This not only saves the time of the experimenters, but also saves the time of the observers who can participate in several different testing methods at one sitting and enter there results electronically.

A GUI scheme is used to automate experiment preparation and sample generation. The invention automates the preparation process based upon the information entered by the experimenter and test methods chosen. The invention then generates and randomizes the print samples for each individual observer. Moreover, the invention allows experimenters to download digital samples to the program and correlate the hard copy used in the experiment with the digital file in the window by use of dynamic links. This ensures that observers are viewing the right samples in the absence of experimenters.

In the following description, reference is made to the accompanying drawings which form a part hereof, and which illustrate several embodiments of the present invention. It is understood that other embodiments may be utilized and structural and operational changes may be made without departing from the scope of the present invention.

FIG. 1 illustrates a computing environment in which preferred embodiments are implemented. The preferred embodiment psychophysics testing system is implemented in a computer program that runs in a plurality of computers 101, 102, 103, and 104. These computers 101–104 may be any computer device known in the art, such as a desktop computer, laptop computer, workstation, mainframe, server, personal digital assistant (PDA), etc. The computers 101–104 would include an operating system 8 such as AIX, OS/390, UNIX, OS/2, MVS, WINDOWS NT, 95/98, LINUX, etc.** A network system 105 links computers 101–104. Network 105 may be comprised of any suitable network architecture known in the art, such as LAN, Ethernet, WAN, Token Ring, LocalTalk, the Internet, etc. Alternatively, there may be separate and different networks between computers 101–104.

Computers 101–104 may include attached display monitors 101A–104A, which may be any suitable device known in the art. An input device (not shown) would also be provided with computers 101–104 to allow the examiners and observers to enter data into computers 101–104. This input device may be comprised of any input means known in the art, including a mouse, keyboard, touch screen display, voice activated input, electronic pen, etc.

In this embodiment, computers 101–104 are divided into an experimenter's station and the observers' stations. The experimenter uses computer 101 to set up and administer the testing. Computers 102–104 are used by the observers in taking the test. It can be appreciated that the testing system need not consist of a plurality of computers. In an alternative embodiment, a single computer could be employed wherein the experimenter would first set up the test and then allow the observer to take the test at the same computer. The test may be designed such that only one observer takes the test at a time. In this way, each observer will view the same print samples, thereby avoiding any variance in the test subject matter presented to the observers. In such case, only one observer computer needs to be available for testing.

Preferred embodiments provide a psychophysics testing tool that uses objects to define both testing layout and the data aspects of the testing. Unlike the prior art, the present invention provides a graphical user interface (GUI) to accomplish all testing steps, including sample generation, randomization, observation, data collection, and analysis. The preferred psychophysics tool is comprised of three program components: a Test Set-Up Program for sample generation and randomization; a Test Administration Program for sample observation and data collection; and a Data Analysis Program for statistical calculations and analysis of the data as well as the display of the test results.

FIGS. 2–6B illustrate GUIs displayed on the display monitors 101A–104A, which guide the experimenter and the observers through these three programs. The Test Set-Up Program begins by displaying the GUI panel shown in FIG. 2 in which an experimenter, i.e., the person designing the experiment, may enter the parameters of a new psychophysics experiment. GUI panel 200 includes the following objects: NAME text box 201, NUM SETS drop down box 202, METHODS selection box 203, OBJECTS selection box 204, SAMPLES selection box 205, CATEGORIES selection box 206, PICS button 207, and NEXT button 208.

The experimenter enters: the name or title of a test in the NAME text box 201, e.g., "algotest;" the number of tests to be performed in the NUM SETS box 202, such as 2 sets; the particular type of psychophysics tests are selected in the METHODS box 203, e.g., "Paired" and "Category," corresponding to the Paired Comparison and Categorical Scale testing methods previously described.

On the right half of the screen of GUI panel 200 are two selectable tabs, labeled TEST 1 and TEST 2. In this instance, TEST 1 is selected. The SAMPLEs panel 205 indicates that the experiment is being set up for the observer to compare printed images of a bird and a house in various combinations. Although not depicted, a selection of TEST 2 would result in setting up the experiment for a comparison of printed text from computer printers of various brands.

OBJECTS box 204 is used to select the algorithms which are used to generate the samples that are subject to comparison. In the test being built in GUI panel 200, the experimenter is going to analyze user preference of the output of the four algorithm to determine which algorithm produces the most desirable print quality. The number of total samples to compare is a function of the number of samples indicated in the SAMPLES box 205 and the number of different algorithms used to generate the samples, as indicated in the OBJECTs box 204. In the test being built in GUI panel 200, the observer will be shown four images of a bird and four of a house, each image generated with one of the four algorithms.

The PICS button 207 is selected for the user to enter the location of an image file, e.g., jpg, .bmp, .pcx, that will comprise the displayed samples. For example, if "bird" was selected in SAMPLES box 205, the experimenter could associate an image file of that bird by selecting PICS 207.

The CATEGORIES box 206 is used in connection with the Categorical Scale psychophysics test. Thus this box enables the experimenter to enter the category descriptions which will be available to the observer and from which the observer may select to best describe the quality of the image being perceived.

After all of the information for Test 1 is completed, the experimenter selects TEST 2 tab. This will result in a new pane on the right side of WINDOW 200 for entering data for the second test. Although not shown, the data for this example will be a comparison of text generated from three different printers.

Figure 3A:
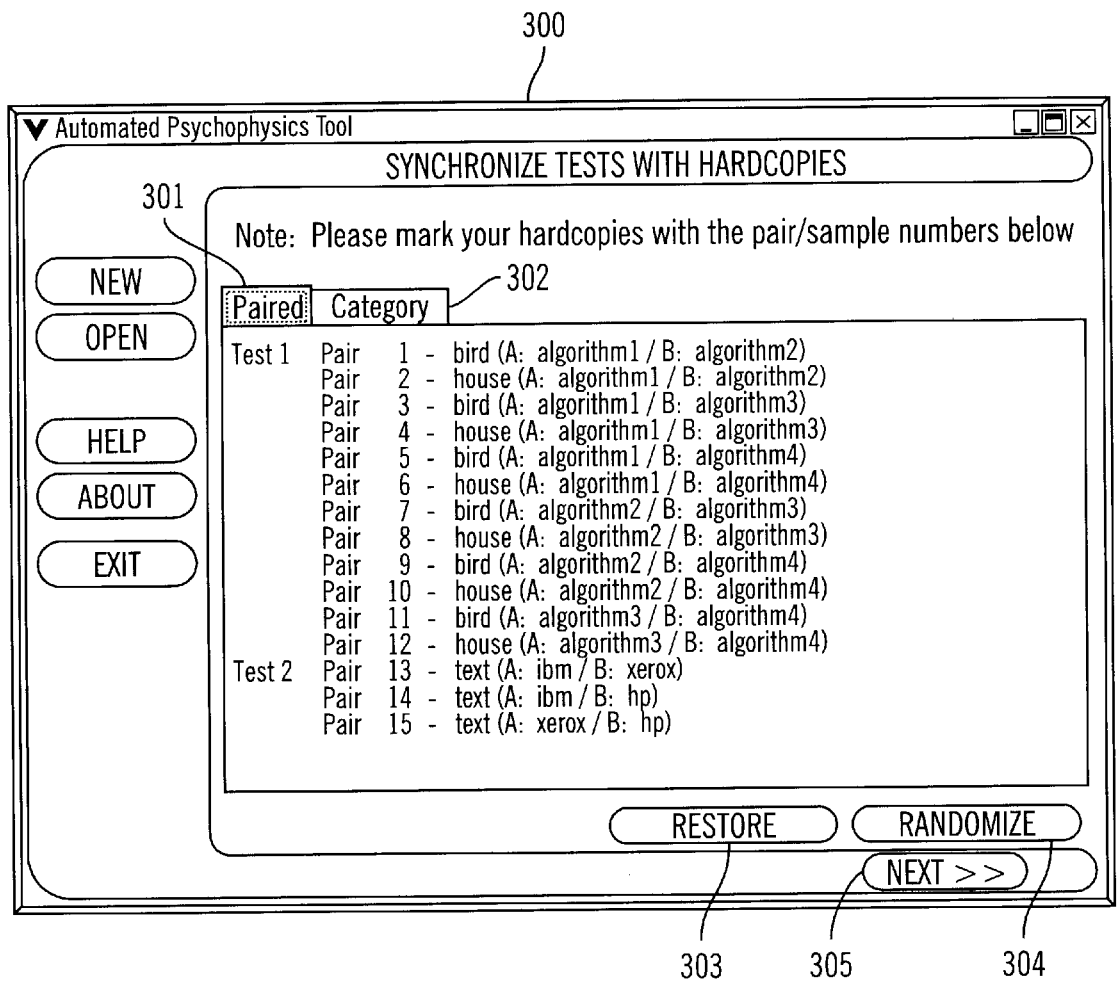

When all required information is entered for the test being built in GUI panel 200 the experimenter selects the NEXT button 208, to advance to GUI panel 300 in FIG. 3A. The panel 300 displays a window 301 which displays a PAIRED tab 301, CATEGORY tab 302, RESTORE button 303, RANDOMIZE button 304, and NEXT button 305.

When the experimenter selects the PAIRED tab 301, the computer generates a listing, as shown, of all possible combinations of pairs of each type of sample for showing to the observer during the Paired Comparison psychophysics test. In this way, the computer provides every paired combination for the bird image generated with the four different algorithms and the house image generated with the four different algorithms, which creates twelve different paired combinations for the eight different images. Pairs are created using the same image type and different algorithms. Different image types are not paired together. Further, the computer assigns a sample or pair number to each combination of image and algorithm, for the total number of images and algorithms to be compared.

The experimenter will take the hard copy printouts of the bird image which was printed using algorithm 1 and the bird image which was printed with algorithm 2, and will mark each of the hard copies with the designations "Pair 1A" and "Pair 1B," respectively. The experimenter will continue this process for Test 1 consisting of all 12 possible pair combinations of bird and house images which were printed using the four computer printer algorithms. Thus, GUI panel 300 automates the process of determining how to order the images to compare.

Similarly for Test 2, the experimenter will take hard copy printouts of the text which was printed using different brand printer, e.g., IBM and Xerox, and mark each of the hard copies with the designations "Pair 13A" and "Pair 13B," respectively. The experimenter will continue this process for pairs 14 and 15 which represent all possible pairings of text samples generated from three different printers.

When this is completed, the experimenter will select CATEGORY tab 302 Although not shown, this will result in a display by GUI panel of the assignment of sample numbers for conducting the Categorical Scales psychophysics test. In the "Category" test, pairings are not used. Rather each printer sample is viewed by the observer individually and assigned a category ranking in comparison with a provided sample. Thus the computer would simply assign a sample number to each bird and house image generated by each of the four algorithms as well as a sample number to each text example generated by each make of printer. As before, the experimenter would label the hard copy print outs of each of these items with the assigned sample numbers.

When this labeling process is completed, the experimenter would next select the RANDOMIZE button 304. This causes computer 101 to randomize the list of test samples using any one of a number of algorithms which are well known in the art and which are capable of generating random numbers and randomizing a list of items.

Figure 3B:
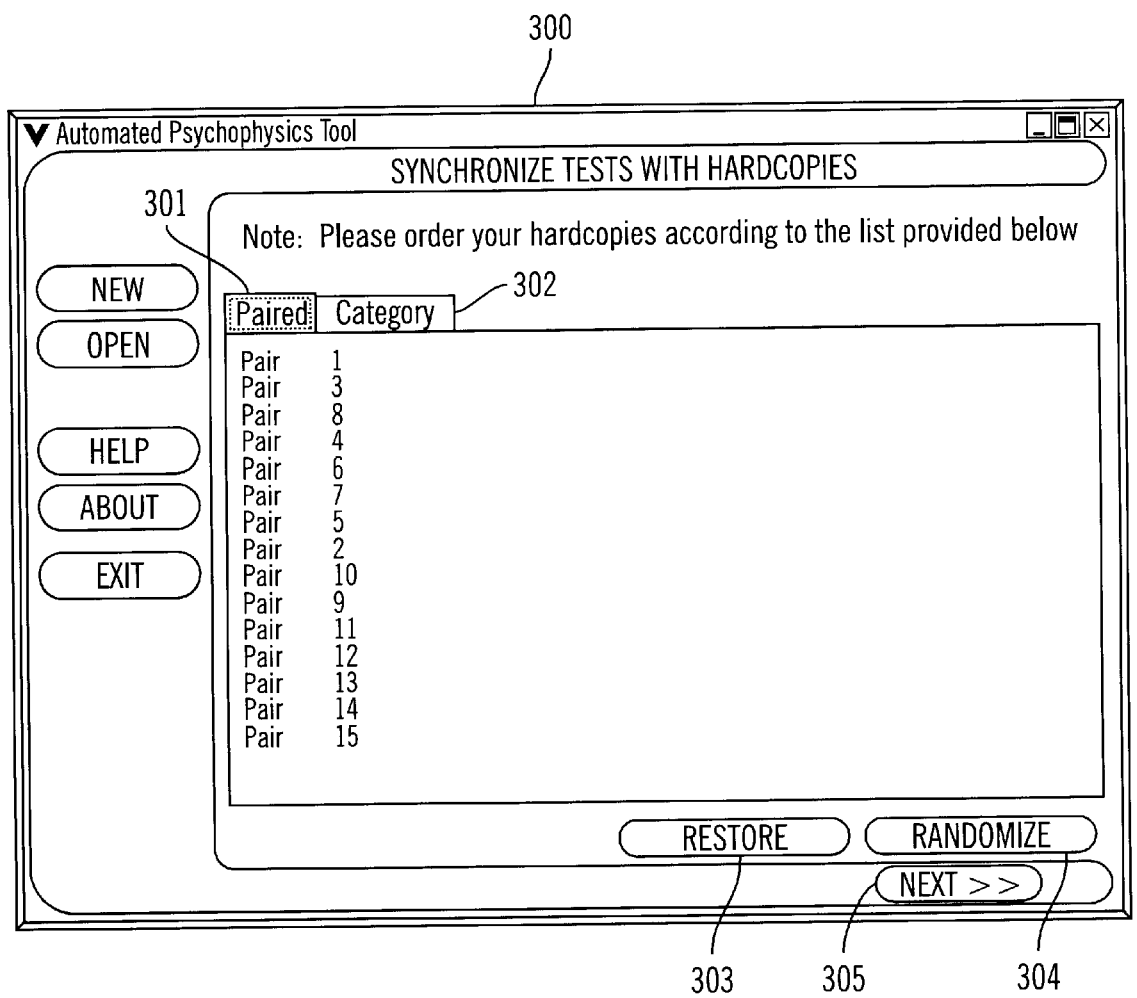

In psychophysics testing involving several observers, it is frequently desirable to display the samples in a different order for each observer. This provides statistically more reliable results. FIG. 3B illustrates a layout for GUI panel 300 after the user selected the RANDOMIZE 304 pushbutton which is used to guide the experimenter in arranging the test samples in random order for a particular observer who will view the samples at one of the obersver stations 102–104. The panel 300 in FIG. 3B includes the same objects as described for FIG. 3A. The only difference between the displays of FIG. 3A and FIG. 3B is that the latter contains a display of the samples in random order. The screen further instructs the experimenter to order the hard copies according to the randomized list.

RESTORE button 303 can be selected at any time and causes the computer to restore the randomized order of samples to the original numerical order of samples shown in FIG. 3A.

Although not shown, the samples used for the Categorical Scale psychophysics test can be randomized. CATEGORY tab 302 is selected which initially will show the samples in numerical order for the Categorical Scale test. After the hard copies are labeled with the appropriate sample number, RANDOMIZE button 304 is selected. As described above, the computer will generate a randomized list of the samples, and the experimenter will be instructed to order the sample hard copies in the random order shown on the screen.

When this process is completed for all tests to be conducted, NEXT button 305 is selected. This will invoke the Test Administration Program whereupon the test setup information will be transferred from computer 101 to one of computers 102–104 via network 105.

Figure 4:
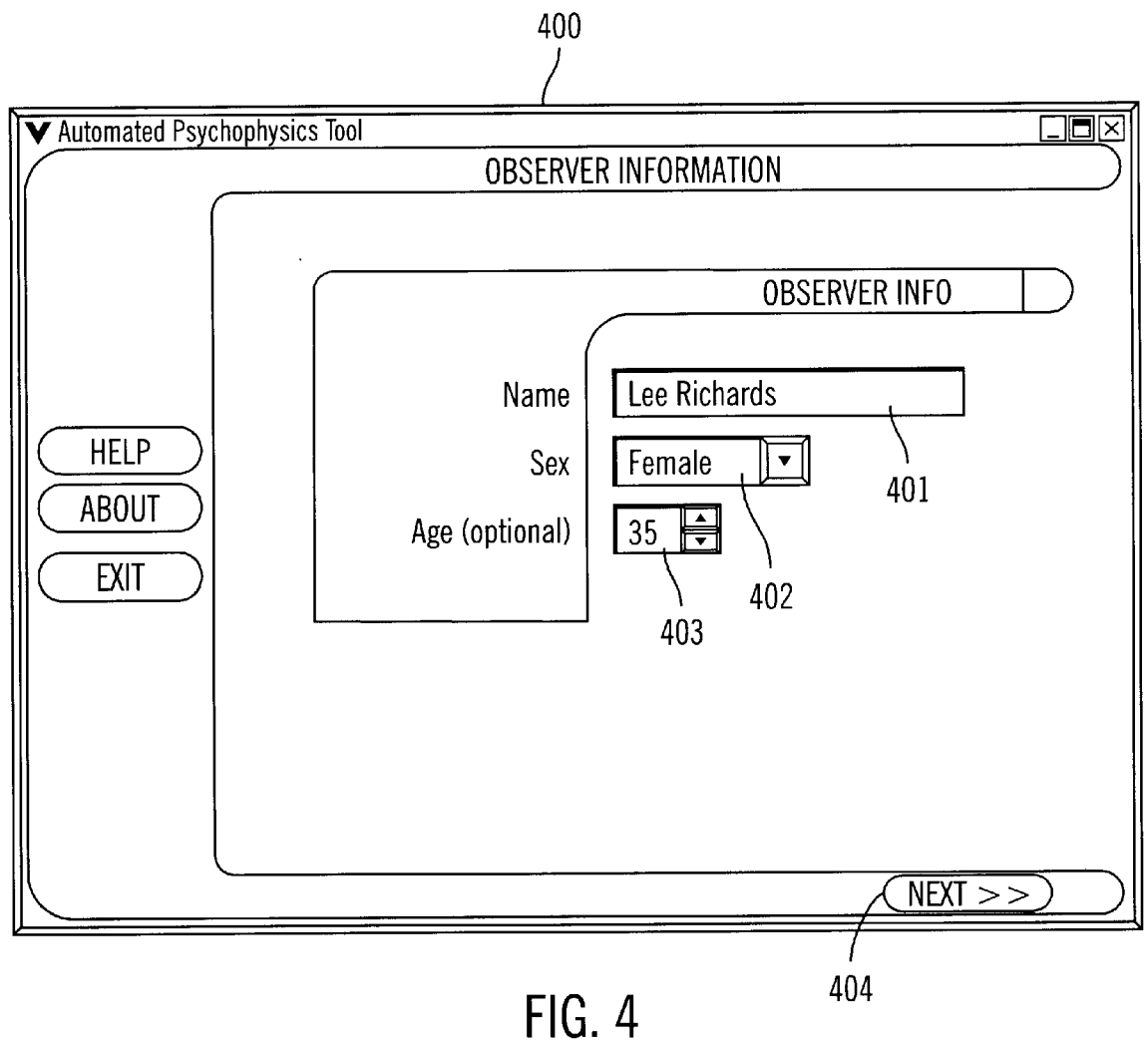
FIGS. 4, 5A, and 5B illustrate graphical user interface (GUI) panels displayed on a computer monitor to receive observer input during a psychophysics experiment in accordance with preferred embodiments of the present invention.

The Test Administration Program begins by displaying GUI panel 400 (FIG. 4) on of one of the monitors 102A–104A to gather information about a test subject. It should be noted that all previous windows illustrated in FIGS. 2–3B were for use by the experimenter. FIG. 4 however is the first window which is seen by the observer. In this example, panel 400 includes the following objects: NAME text box 401, SEX text box 402, AGE text box 403, and NEXT button 404. However, it can be appreciated that panel 400 could be designed to include a great deal of other demographic information about each observer. Upon entering the demographic information in text boxes 401, 402 and 403, the observer selects NEXT button 404 to advance to GUI panel 500 in FIG. 5A.

Figure 5A:
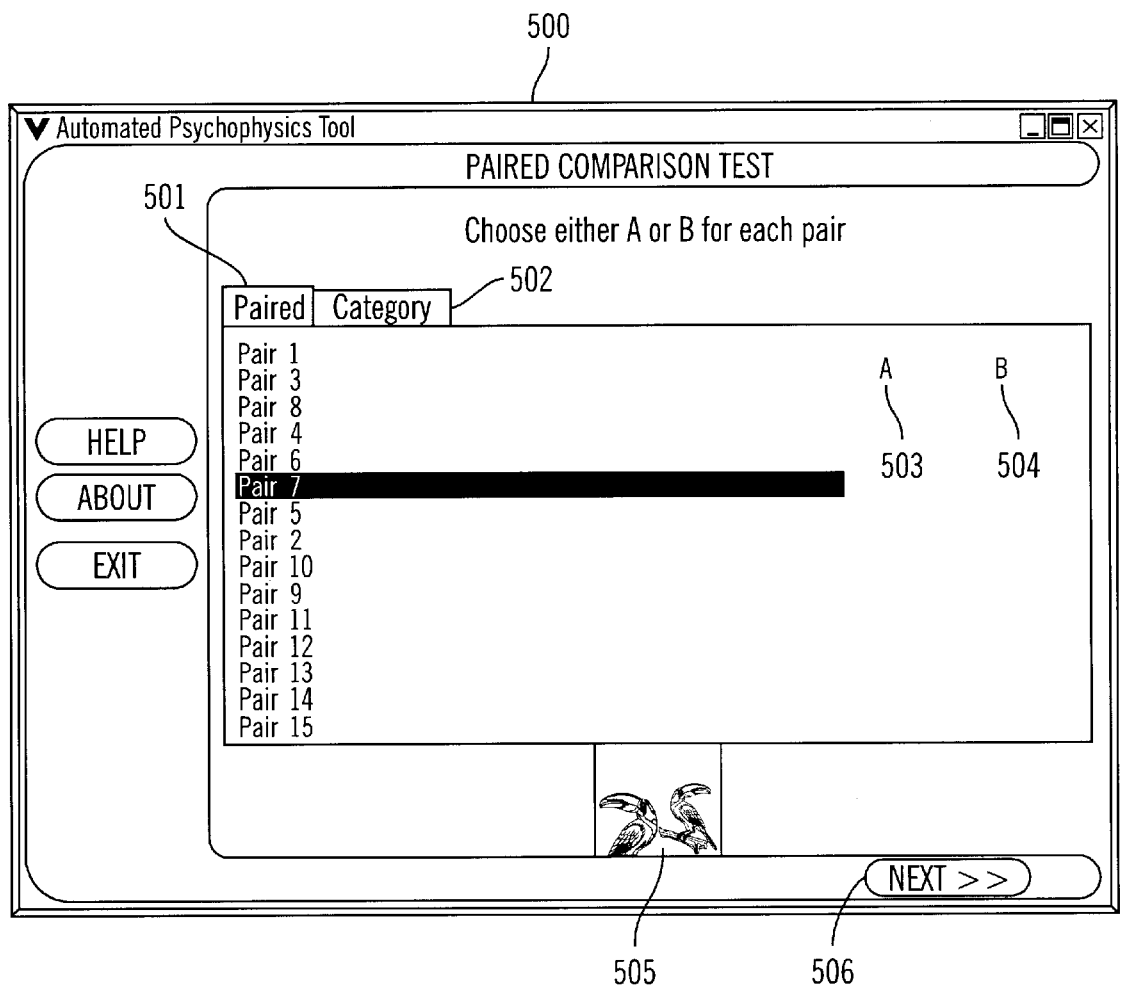

The panel 500 in FIG. 5A is displayed to the test observer to receive input for the observer's psychophysical response to each sample. Panel WINDOW 500 includes the following objects: PAIRED tab 501, CATEGORY tab 502, "A" button 503, "B" button 504, image 505, and NEXT button 506.

Upon selecting PAIRED tab 501, the observer is presented with a screen showing the randomized pair combinations in the order in which they are to be observed for the Paired Comparison test. The randomized pair combinations are in the same order as shown in FIG. 3B. The observer first selects "Pair 1" on the screen. Next the observer views the hard copy images in his possession which were previously marked "Pair 1 A" and "Pair 1B" by the experimenter. The observer compares the two images which constitute Pair 1 and selects either "A" button 503 or "B" button 504, whichever corresponds to the hard copy image deemed by the observer to be of the higher quality.

The observer proceeds down the randomized list, next selecting Pair 3 on the screen, followed by Pair 8, and so on. At each step, the observer selects either image "A" or "B" and records his preference by selecting button 503 or 504. For each pair selected on the screen, image 505 is displayed. Image 505 is an on-screen counterpart image to the hard copy samples which are being tested. This serves as a cross check for the observer so that the observer can verify that the hard copy samples being viewed do in fact correspond to the computer designation for such pairs. In the example shown in FIG. 5A, pair 7 has been selected. IMAGE 505 is an image of a pair of birds. Thus the observer can readily see whether his hard copy pair number 7 also consists of images of birds. If they do not, then the experiment can be halted until the randomized order and labeling of the hard copy samples are verified.

Figure 5B:
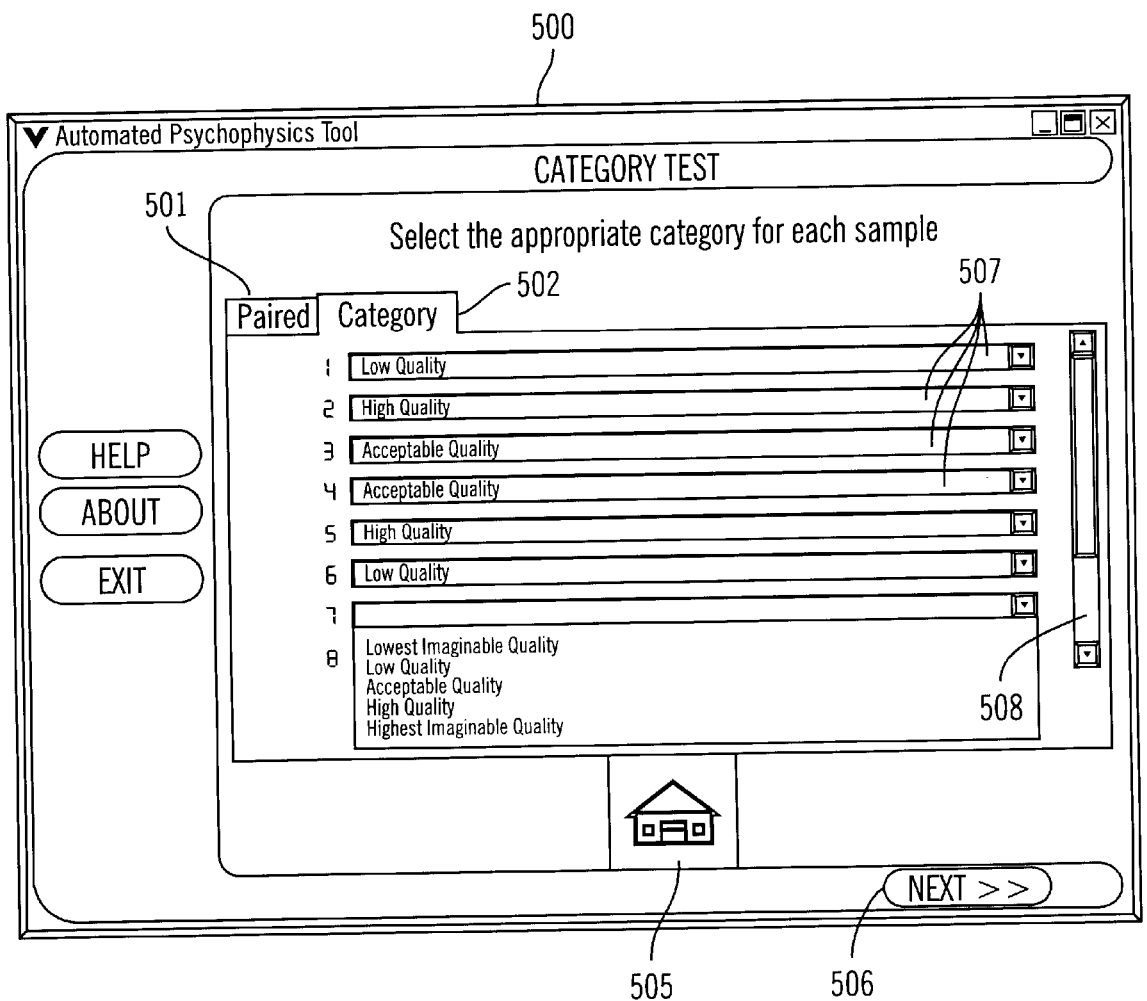

After completing the paired comparison test, the observer would next select the CATEGORY tab 502 in order to conduct the Categorical Scale psychophysics test. FIG. 5B illustrates a GUI panel 500 for conducting the Categorical Scale test. Panel 500 displays an entry field 507 for each different image, e.g., bird and house, printed using the four different algorithms. Each entry field 507 includes a drop down box including different categorical selections the user would select as the response to the image.

In conducting the Categorical Scale test, the observer would view the hard copy image which has been labeled "Sample 1 " and select one of the descriptions available in the drop down boxes 507 which corresponds to Sample 1. In the example shown in FIG. 5B, the observer selected the "Low Quality" category for Sample 1, "High Quality" for sample 2, etc.

The observer proceeds down all of the samples in a similar fashion. Scroll bar 508 allows the observer to record his categorizations as to further hard copy samples until all have been viewed. When the Categorical Scale test is complete, NEXT button 506 is selected. This accomplishes several things. First, the data recorded by the observer is sent via network 105 to computer 101, the experimenter's station. There the data is stored in the program's database, where a user's data is related to the user, the test, and the type of test. The Data Analysis Program component would then retrieve the data from the database and performs statistical calculations on the data. In alternative embodiments, the data is not stored in a database structure. Rather, it can be stored in any other format or structure which will allow the computer to use the data and perform the necessary calculations.

Figure 6A:
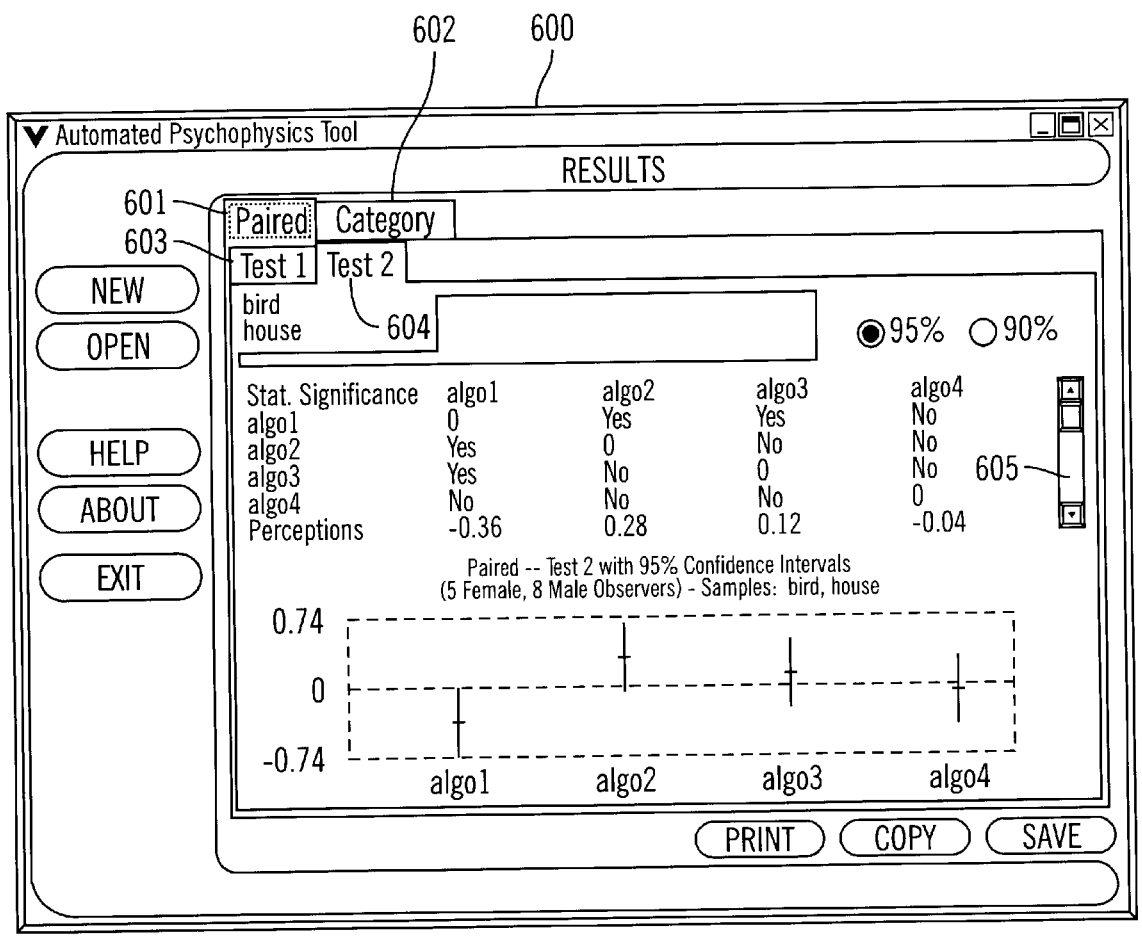
FIGS. 6A and 6B illustrate graphical user interface (GUI) panels displayed on a computer monitor including statistical analysis of the psychophysics data entered by the observer.
Figure 6B:
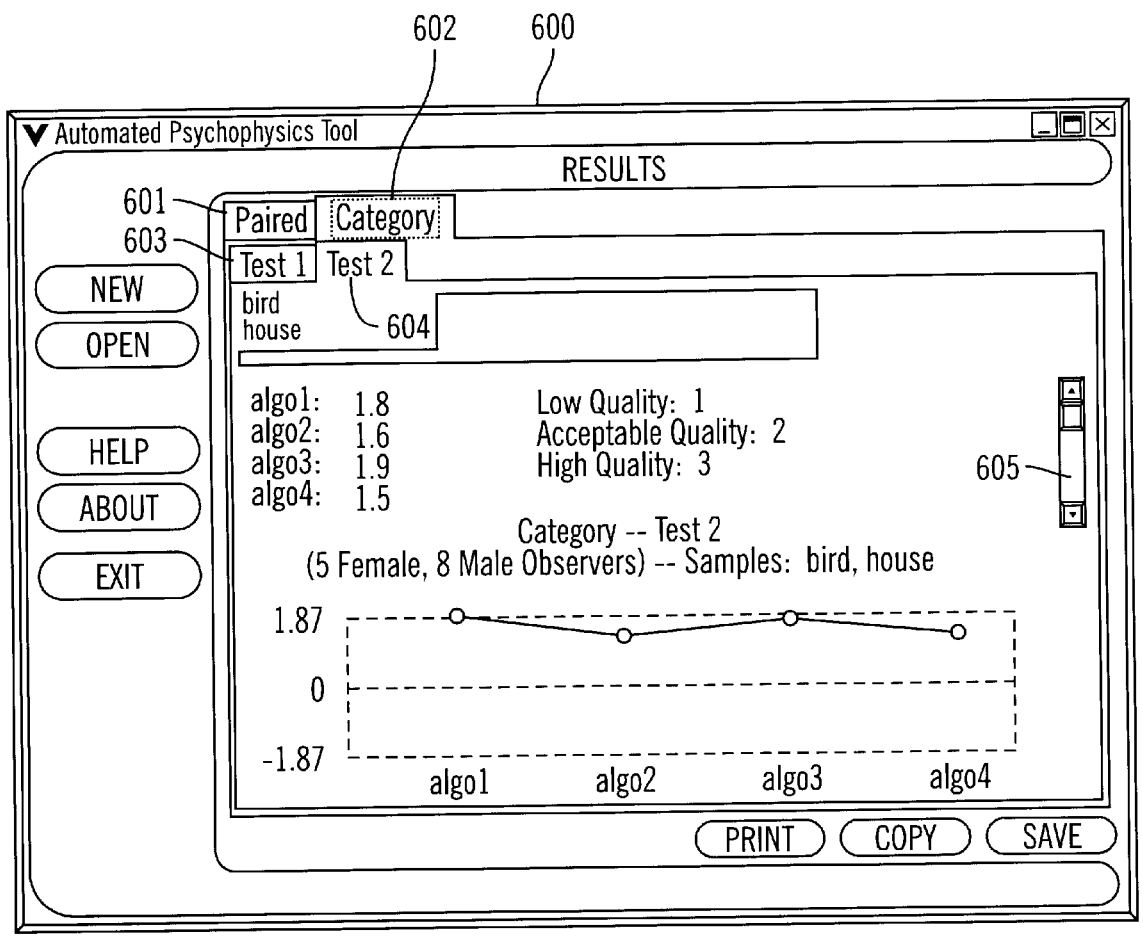

The Data Analysis Program would then perform known psychophysics statistical analysis on the data collected using the GUI panels. FIGS. 6A and 6B illustrate displays of statistical test results to the experimenter. Panel 600 includes the following objects: PAIRED tab 601, CATEGORY tab 602, TEST 1 tab 603, TEST 2 tab 604, and scroll bar 605.

In FIG. 6A, PAIRED tab 601 and TEST 2 tab 603 have been selected. Thus displayed are the statistical testing results for the psychophysics Paired Comparison test involving the images of a bird and a house which were generated by the four printer algorithms. Had TEST 1 tab 603 been selected, then the Paired Comparison results involving the text generated by three printers would have been displayed. Scroll bar 605 is used for those instances when there are additional statistical test results for viewing which correspond to the visual display in question. Moreover, selection of the COPY/PRINT/SAVE button lets one of these actions to be taken with respect to the displayed statistical information. Selection of the COPY button would copy the statistical data and graphics to any word processor or other similar type program to save as a file, selection of PRINT would print the displayed statistical data, and SAVE would save the data.

In FIG. 6B, Window 600 reflects the selection of CATEGORY tab 602 and TEST 2 tab 604. Thus displayed are the statistical testing results for the psychophysics Categorical Scale test involving the images of a bird and a house which were generated by the four printer algorithms. Had TEST 1 tab 603 been selected, then the Categorical Scale test results involving the printer text would have been displayed. The statistical results can be generated based on the data for each image separately. For instance, the statistical results may be reviewed for the data generated from the display of the images of the bird and house, separately. Alternatively, the statistical results may be provided for any combination of images used in the experiment for which data was gathered. This allows the experimenter to present images with different print qualities, and then separately review statistics on observer responses to the images having different print qualities.

Operation of Interface

Figure 7:
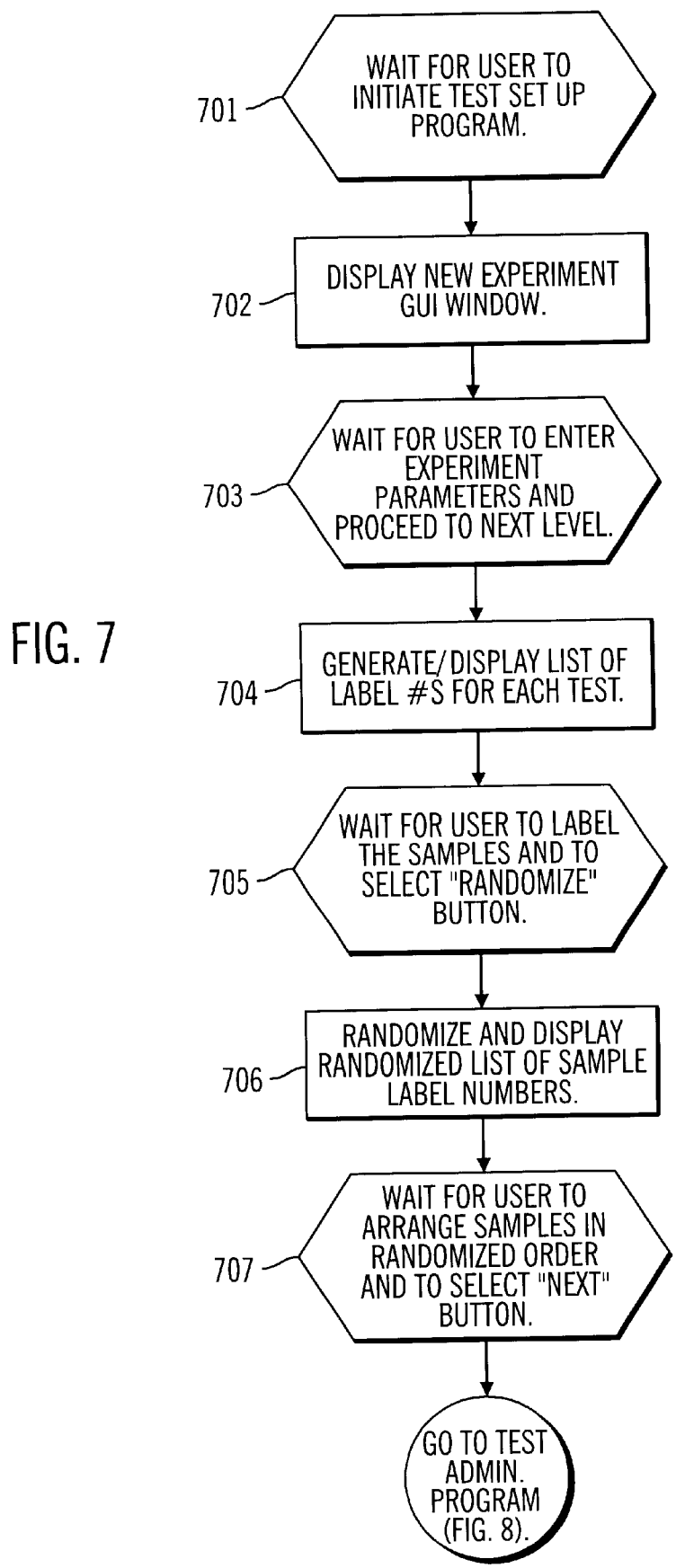
FIG. 7 illustrates logic to set up a psychophysics test for later test administration in accordance with preferred embodiments of the present invention.
Figure 8:
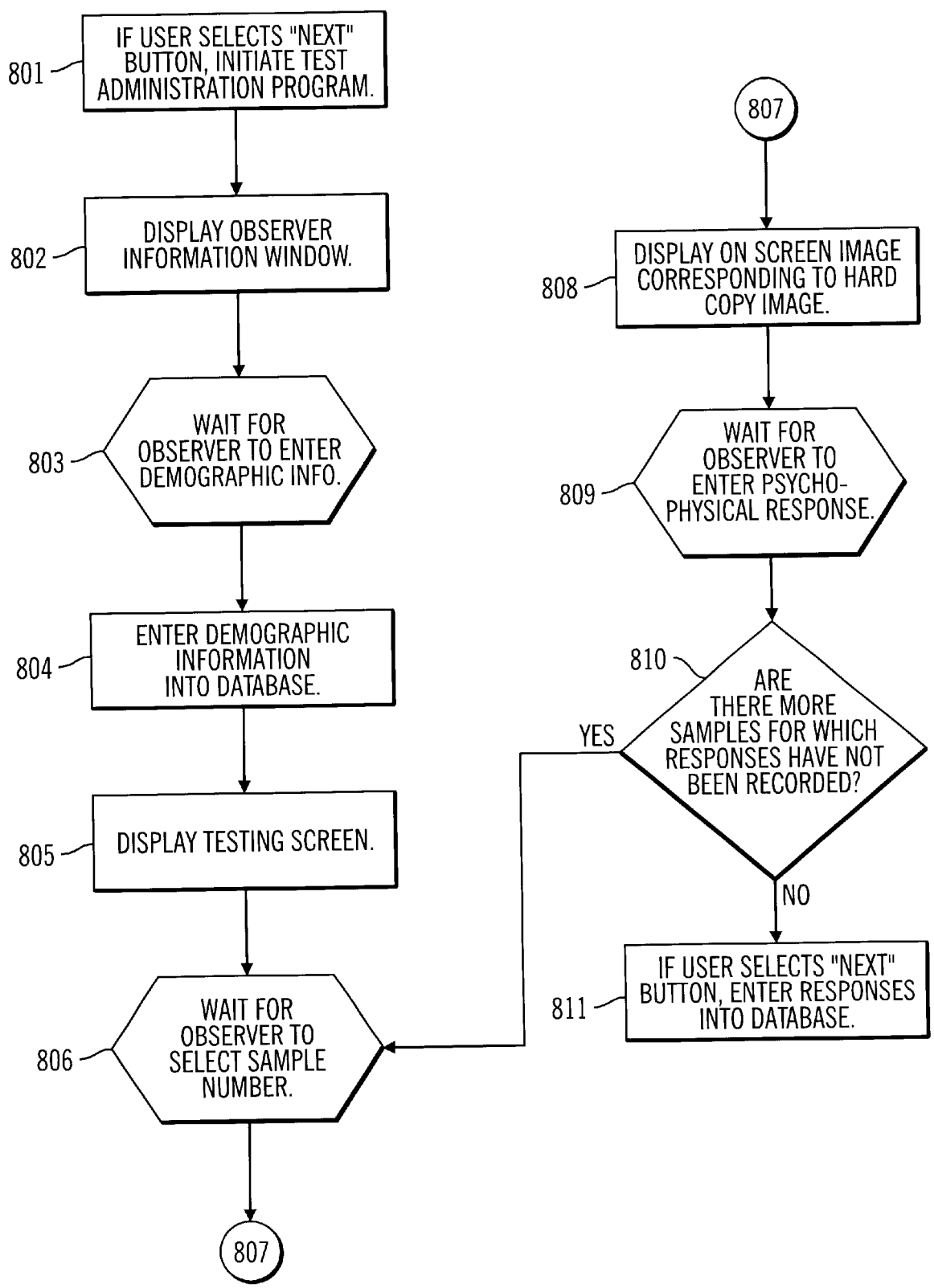
FIG. 8 illustrates logic to administer a psychophysics test in accordance with preferred embodiments of the present invention.
Figure 9:
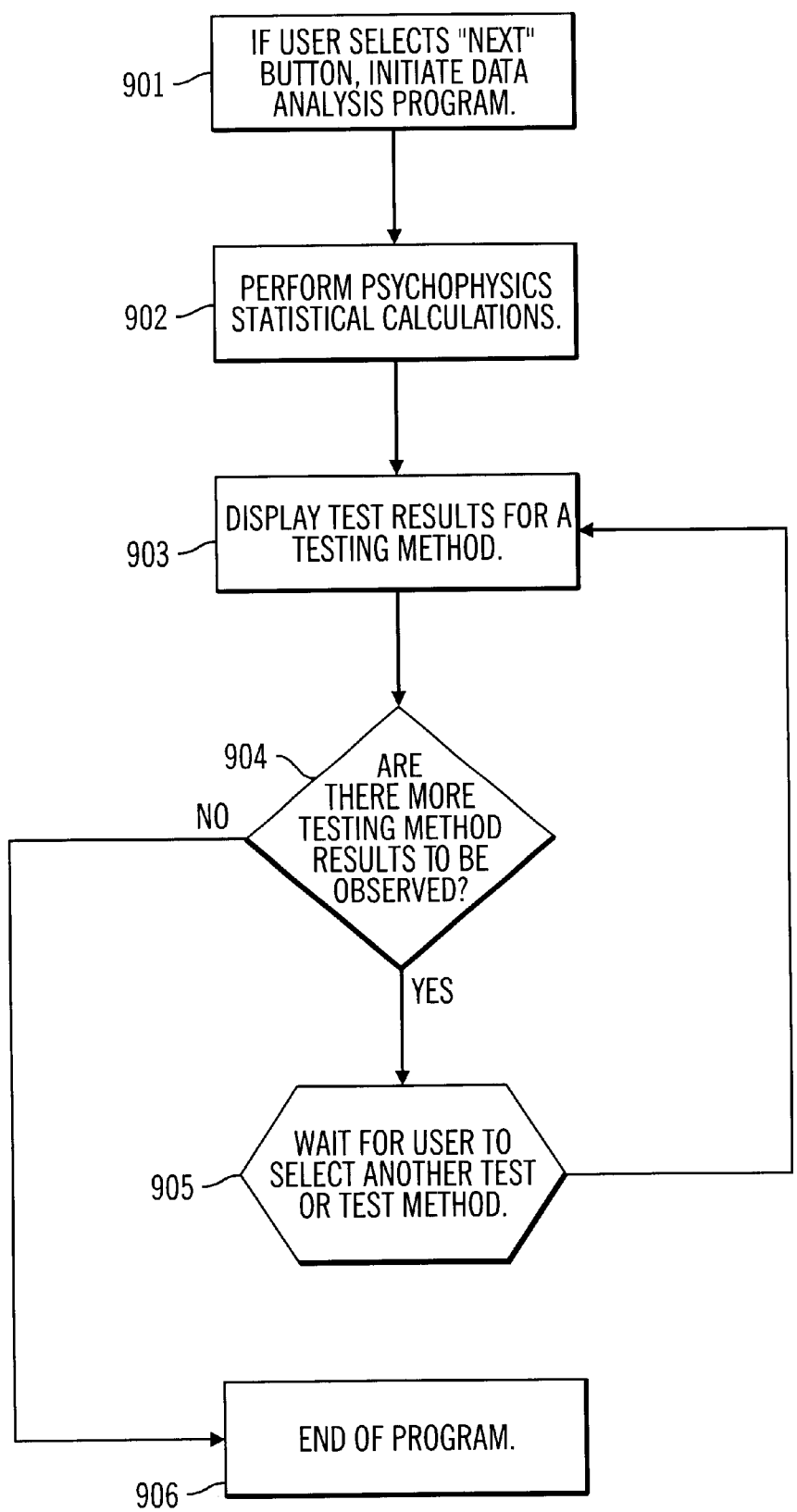
FIG. 9 illustrates logic to analyze the psychophysics test data in accordance with preferred embodiments of the present invention.

FIGS. 7–9 illustrate program logic implemented in computers 101–104 within an application program to conduct the psychophysics testing and analysis. The logic of FIGS. 7–9 may generate GUI interfaces to sequence (1) the experimenter through a series of steps in setting up the testing parameters, (2) the observers in recording their observations, and (3) the experimenter in reviewing the testing results.

Referring to FIG. 7, control begins at block 701 which represents computer 101 waiting for an experimenter to invoke the psychophysics program application. Control transfers to block 702 where computer 101 displays a new experiment window, such as window 200 shown in FIG. 2, and then to block 703 where the computer waits for the experimenter to enter the experiment parameters such as, for example, the selection of psychophysics testing methods to be used, the number of tests to be run, the identity of the samples which are to be observed, etc.

When the experimenter enters all parameters and selects NEXT button 408, control transfers to block 704 where computer 101 generates and displays a list of all samples along with their label number assignments for each type of test to be conducted as shown in FIG. 3A. Control transfers to block 705 where the computer waits for the experimenter to complete labeling the hard copy samples with the assigned label numbers and to select RANDOMIZE button 304.

Upon selecting RANDOMIZE button 304, control transfers to block 706 where the computer randomizes the order of the sample label numbers and displays the randomized order as shown in FIG. 3B. Control then transfers to block 707 where the computer waits for the experimenter to arrange the samples in the randomized order displayed on computer monitor 101A and to select NEXT button 305.

Selecting NEXT button 305 will initiate the Test Administration Program portion of the invention. FIG. 8 illustrates logic implemented in computers 101–104 within an application program to conduct the psychophysics test administration. The program's control initiates at block 801. Control transfers to block 802 which causes the computer to display an observer information screen such as that shown in FIG. 4. Control then transfers to block 803 where the computer waits for the observer to enter the requested demographic data. Upon completion of the entering of this data, the observer selects NEXT button 404.

Control then transfers to block 804 where the computer enters and stores the demographic data into the database portion of the program. Control transfers to block 805 where the computer displays a test screen such as Window 500 in FIG. 5A. Control transfers to block 806 where the computer waits for the observer to select the first sample in the randomized list of samples to be viewed. Upon the observer selecting (or "hi lighting") a sample, control transfers to block 808 where the computer displays on-screen image 505 which should correspond to the hard copy sample being observed. As previously discussed, this serves as a cross check for the observer to verify that the labeled hard copy sample being viewed does indeed correspond with the label number on the screen.

Control transfers to block 809 where the computer waits for the observer to record a selection which reflects the observer's psychophysical response to the sample. In FIG. 5A, the option is to select either button A 503 or button B 504, whichever corresponds to the better quality of the two images of a bird printed by different printer algorithms.

Block 810 represents a decision loop. If there are additional samples in Window 500 to be viewed by the observer, control returns to block 806 where the observer will select the next sample on the randomized list. However, if there are no additional samples to be viewed, then control transfers to block 811 where the computer waits for the observer to select NEXT button 506. Upon selection of NEXT button 506, control shifts to block 811 where the computer stores all of the observer's selections into the program's database or other data structure thus concluding the Test Administration portion of the program. In preferred embodiments, the observer must enter all responses for all possible tests before the program will proceed to the next stage of the Data Analysis Program.

Selecting NEXT button 506 also will initiate the Data Analysis Program portion of the invention. FIG. 9 illustrates logic implemented in computers 101–104 within an application program to conduct the psychophysics data analysis. The program's control initiates at block 901. Control transfers to block 902 which causes the computer perform the psychophysics statistical calculations using the previously stored data.

Control then transfers to block 903 where the computer displays a test results information screen such as that shown in Window 600 in FIG. 6A. Block 904 represents a decision loop with respect to test results selections. If there were more than one psychophysics test conducted, as was the case depicted in FIG. 6A, then the experimenter must decide whether he desires to observe other test results. If so, control would transfer to block 905 where the computer would wait for the experimenter to select another test or test method. In FIG. 6A, this would be accomplished by selecting tabs 601, 602, 603, or 604. Upon selecting one of these tabs, control would return to block 903 where the process would be repeated and a different test results screen, such as for example, FIG. 6B, would be displayed. Returning to block 904 however, if there are no other test results which are to be viewed, then the Data Analysis Program is completed.

Conclusions and Alternative Embodiments

This concludes the description of the preferred embodiments of the invention. The following describes some alternative embodiments for accomplishing the present invention.

The preferred embodiments may be implemented as a method, apparatus or article of manufacture using standard programming and/or engineering techniques to produce software, firmware, hardware, or any combination thereof. The term "article of manufacture"(or alternatively, "computer program product") as used herein is intended to encompass one or more computer programs and data files accessible from one or more computer-readable devices, carriers, or media, such as a magnetic storage media, "floppy disk," CD-ROM, a file server providing access to the programs via a network transmission line, holographic unit, etc. Of course, those skilled in the art will recognize that many modifications may be made to this configuration without departing from the scope of the present invention.

Preferred embodiments described different experimenter and observer stations. In alternative embodiments, the experimenter station may be later used as an observer station.

The observer stations were described as personal computers. In further embodiments, the observer stations may comprise a basic input means and display device, without using a separate, stand-alone computer. In such case, entered data may be transmitted directly to the experimenter's station. Alternatively, the test may be administered remotely, where the observer stations are at remote locations.

In preferred embodiments, the subjects of the experiment were described as printer output printed according to different printing algorithms. However, the preferred embodiments for defining and administering a psychophysics experiment may apply to samples in any type of media, including text, images, sounds, motion pictures, etc. The observable samples that are the subject of the tests are not limited to print samples. In the event that samples in other types of media are used, the algorithms would be designed to generate output in that media type and would be the subject of the comparison.

In summary, preferred embodiments provide a method, system, and program for method, system, and program for defining and administering a test to determine human perceptions of observable samples. A displayable test building window includes input fields to receive input on at least one observable sample according to at least one type of experiment. Generated in a data gathering window is at least one perception input field for each observable sample and at least one type of experiment. The observer is capable of entering perception information in each input field concerning the observable samples. Observer perception input on the observable samples is received and stored. Statistical analysis is then performed on the entered perception input.

The foregoing description of the preferred embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method for defining and administering a test to determine human perceptions of observable samples, comprising:

displaying a test building window including input fields to receive input on at least one observable sample according to at least one type of experiment;

generating in a data gathering window at least one perception input field for each observable sample and at least one type of experiment, wherein the observer is capable of entering perception information in each input field concerning the observable samples;

receiving observer perception input on the observable samples;

storing the observer entered perception input; and performing statistical analysis of the entered perception input.

2. The method of claim 1, wherein the type of experiment is a member of the set of experiments consisting of paired comparison, ranking order, categorical scale, rating scale, ratio scale, and probit analysis.

3. The method of claim 1, wherein the observable same is embodied in a medium that is a member of the set of mediums comprising: images, text, sound, and motion pictures.

4. The method of claim 1, wherein displaying the test building window comprises displaying a plurality of different types of experiments which the user selects to include in the test, and wherein generating the input field in the data gathering window comprises generating at least one input field for each observable sample and each type of experiment the user selects.

5. The method of claim 4, wherein the test building window further displays an algorithm field indicating at least one algorithm used to generate each observable sample, wherein generating the input field in the data gathering window further comprises generating at least one input field for each observable sample printed according to each algorithm displayed in the algorithm field.

6. The method of claim 5, wherein the algorithm comprises a printing algorithm to control a printer to print the observable sample on paper.

7. The method of claim 5, wherein at least one experiment type comprises a categorical scale experiment, wherein displaying the test building window further comprises displaying multiple quality levels, and wherein generating in the data gathering window each input field further comprises generating the capability to select one of the multiple quality levels displayed in the test building window to enter into the input field for each observable sample printed according to one algorithm displayed in the algorithm field.

8. The method of claim 5, wherein the experiment type includes a paired comparison experiment, wherein the observable samples comprise at least one sample printed according to at least two algorithms, further comprising displaying a paired comparison window listing each possible combination of pairs of the same sample printed using different algorithms, and wherein generating the input field in the data gathering window further comprises generating an input field for each comparison pair to receive user input on the perceived higher quality observable same for each comparison pair.

9. The method of claim 8, further comprising displaying a randomize pushbutton in the paired comparison window capable of causing the display of the pairs of samples in a random order indicating an order of presenting the observable samples to a test observer.

10. A system for defining and administering a test to determine human perceptions of observable samples, comprising;
   a computer system;
   program logic executed by the computer system; comprising:
      (i) means for displaying a test building window including input fields to receive input on at least one observable sample according to at least one type of experiment;
      (ii) means for generating in a data gathering window at least one perception input field for each observable sample and at least one type of experiment, wherein the observer is capable of entering perception information in each input field concerning the observable samples;
      (iii) means for receiving observer perception input on the observable samples;
      (iv) means for storing the observer entered perception input; and
      (v) means for performing statistical analysis of the entered perception input.

11. The system of claim 10, wherein the computer system comprises:
   a first computer implementing the program logic for displaying the test building window, storing the observer entered perception input, and performing the statistical analysis; and
   a second computer implementing the program logic for generating the data gathering window and receiving observer perception input; and
   a communication link providing communication between the first and second computers to allow the transfer of observer perception input from the second computer to the first computer.

12. The system of claim 10, wherein the type of experiment is a member of the set of experiments consisting of paired comparison, ranking order, categorical scale, rating scale, ratio scale, and probit analysis.

13. The system of claim 10, wherein the observable sample is embodied in a medium that is a member of the set of mediums comprising: images, text, sound, and motion pictures.

14. The system of claim 10, wherein the program logic for displaying the test building window comprises means for displaying a plurality of different types of experiments which the user selects to include in the test, and wherein the program logic for generating the input field in the data gathering window comprises means for generating at least one input field for each observable sample and each type of experiment the user selects.

15. The system of claim 14, wherein the program logic for the test building window further comprises means for displaying an algorithm field indicating at least one algorithm used to generate each observable sample, wherein the program logic for generating the input field in the data gathering window further comprises means for generating at least one input field for each observable sample printed according to each algorithm displayed in the algorithm field.

16. The system of claim 15, wherein the algorithm comprises a printing algorithm to control a printer to print the observable sample on paper.

17. The system of claim 15, wherein at least one experiment type comprises a categorical scale experiment, wherein the program logic for displaying the test building window further comprises means for displaying multiple quality levels, and wherein the program logic for generating in the data gathering window each input field further comprises means for generating the capability to select one of the multiple quality levels displayed in the test building window to enter into the input field for each observable sample printed according to one algorithm displayed in the algorithm field.

18. The system of claim 15, wherein the experiment type includes a paired comparison experiment, wherein the observable samples comprise at least one sample printed according to at least two algorithms, wherein the program logic further comprises means for displaying a paired comparison window listing each possible combination of pairs of the same sample printed using different algorithms, and wherein the program logic for generating the input field in the data gathering window further comprises means for generating an input field for each comparison pair to receive user input on the perceived higher quality observable same for each comparison pair.

19. The method of claim 18, wherein the program logic further comprises means for displaying a randomize pushbutton in the paired comparison window capable of causing the display of the pairs of samples in a random order indicating an order of presenting the observable samples to a test observer.

20. An article of manufacture for use in defining and administering a test to determine human perceptions of observable samples, the article of manufacture comprising computer usable media including at least one computer program embedded therein that causes the computer to perform:
   displaying a test building window including input fields to receive input on at least one observable sample according to at least one type of experiment;
   generating in a data gathering window at least one perception input field for each observable sample and at least one type of experiment, wherein the observer is capable of entering perception information in each input field concerning the observable samples;
   receiving observer perception input on the observable samples;
   storing the observer entered perception input; and
   performing statistical analysis of the entered perception input.

21. The article of manufacture of claim 20, wherein the type of experiment is a member of the set of experiments consisting of paired comparison, ranking order, categorical scale, rating scale, ratio scale, and probit analysis.

22. The article of manufacture of claim 20, wherein the observable sample is embodied in a medium that is a member of the set of mediums comprising: images, text, sound, and motion pictures.

23. The article of manufacture of claim 20, wherein displaying the test building window comprises displaying a plurality of different types of experiments which the user selects to include in the test, and wherein generating the input field in the data gathering window comprises generating at least one input field for each observable sample and each type of experiment the user selects.

24. The article of manufacture of claim 23, wherein the test building window further displays an algorithm field indicating at least one algorithm used to generate each observable sample, wherein generating the input field in the data gathering window further comprises generating at least one input field for each observable sample printed according to each algorithm displayed in the algorithm field.

25. The article of manufacture of claim 24, wherein the algorithm comprises a printing algorithm to control a printer to print the observable sample on paper.

26. The article of manufacture of claim 24, wherein at least one experiment type comprises a categorical scale experiment, wherein displaying the test building window further comprises displaying multiple quality levels, and wherein generating in the data gathering window each input field further comprises generating the capability to select one of the multiple quality levels displayed in the test building window to enter into the input field for each observable sample printed according to one algorithm displayed in the algorithm field.

27. The article of manufacture of claim 24, wherein the experiment type includes a paired comparison experiment, wherein the observable samples comprise at least one sample printed according to at least two algorithms, further comprising displaying a paired comparison window listing each possible combination of pairs of the same sample printed using different algorithms, and wherein generating the input field in the data gathering window further comprises generating an input field for each comparison pair to receive user input on the perceived higher quality observable same for each comparison pair.

28. The article of manufacture of claim 27, further comprising displaying a randomize pushbutton in the paired comparison window capable of causing the display of the pairs of samples in a random order indicating an order of presenting the observable samples to a test observer.

\* \* \* \* \*